(12) United States Patent
Ida

(10) Patent No.: US 9,453,761 B2
(45) Date of Patent: Sep. 27, 2016

(54) PHOTOACOUSTIC WAVE MEASUREMENT DEVICE

(71) Applicant: ADVANTEST CORPORATION, Tokyo (JP)

(72) Inventor: Taiichiro Ida, Gunma (JP)

(73) Assignee: ADVANTEST CORPORATION, Tokyo (JP)

( * ) Notice: Subject to any disclaimer, the term of this patent is extended or adjusted under 35 U.S.C. 154(b) by 128 days.

(21) Appl. No.: 14/382,596

(22) PCT Filed: May 2, 2013

(86) PCT No.: PCT/JP2013/063232
§ 371 (c)(1),
(2) Date: Sep. 3, 2014

(87) PCT Pub. No.: WO2013/183400
PCT Pub. Date: Dec. 12, 2013

(65) Prior Publication Data
US 2015/0075288 A1    Mar. 19, 2015

(30) Foreign Application Priority Data
Jun. 4, 2012   (JP) ................... 2012-127056

(51) Int. Cl.
*G01H 9/00*    (2006.01)
*A61B 5/00*    (2006.01)
(Continued)

(52) U.S. Cl.
CPC ............ *G01H 9/004* (2013.01); *A61B 5/0095* (2013.01); *A61B 5/7203* (2013.01); *G01N 21/1702* (2013.01); *G01N 29/2418* (2013.01); *G01N 2021/1708* (2013.01)

(58) Field of Classification Search
CPC .. A61B 5/7203; A61B 5/0095; G01H 9/004; G01N 21/1702; G01N 29/2418; G01N 2021/1708

USPC .............................................. 73/655; 356/630
See application file for complete search history.

(56) References Cited

U.S. PATENT DOCUMENTS

2007/0015978 A1   1/2007  Kanayama et al.
2010/0053618 A1   3/2010  Nakajima et al.
(Continued)

FOREIGN PATENT DOCUMENTS

CN    102525550    7/2012
JP    2010-125260  6/2010
(Continued)

OTHER PUBLICATIONS

U.S. Appl. no. 14/397,939 to Taiichiro Ida, filed Oct. 30, 2014.
(Continued)

*Primary Examiner* — Michael A Lyons
*Assistant Examiner* — Suman K Nath
(74) *Attorney, Agent, or Firm* — Greenblum & Bernstein, P.L.C.

(57) ABSTRACT

A photoacoustic wave measurement device includes a pulsed-light outputter, an arrangement member and a photoacoustic wave detector. The pulsed-light outputter outputs a pulsed light. The arrangement member is disposed between a pulsed-light output end of the pulsed-light outputter and a measurement object, the arrangement member being adapted to allow the pulsed light to pass therethrough. The photoacoustic wave detector receives a photoacoustic wave generated by the measurement object by the pulsed light and converts the photoacoustic wave into an electric signal. The photoacoustic wave detector is farther from the measurement object than the pulsed-light output end. The arrangement member has such a sufficient thickness that noise to be detected by the photoacoustic wave detector after a start time of detection of the photoacoustic wave starts to be detected after an end time of the detection of the photoacoustic wave.

3 Claims, 3 Drawing Sheets

(51) Int. Cl.
*G01N 29/24* (2006.01)
*G01N 21/17* (2006.01)

(56) References Cited

U.S. PATENT DOCUMENTS

| | | | |
|---|---|---|---|
| 2011/0112391 A1 | 5/2011 | Nishihara et al. | |
| 2011/0194380 A1* | 8/2011 | Fukutani | A61B 5/0095 367/140 |
| 2012/0130222 A1* | 5/2012 | Kobayashi | A61B 5/0095 600/407 |
| 2012/0133941 A1 | 5/2012 | Nakajima et al. | |
| 2012/0325006 A1 | 12/2012 | Suzuki | |
| 2013/0121106 A1 | 5/2013 | Nishihara | |
| 2013/0123604 A1* | 5/2013 | Oyama | A61B 5/0095 600/407 |
| 2014/0307259 A1 | 10/2014 | Ida | |
| 2014/0309515 A1 | 10/2014 | Ida | |
| 2014/0309516 A1 | 10/2014 | Ida | |

FOREIGN PATENT DOCUMENTS

| | | |
|---|---|---|
| JP | 2011-183149 | 9/2011 |
| JP | 2011-229660 | 11/2011 |
| JP | 2012-24460 | 2/2012 |
| JP | 2012-29715 | 2/2012 |
| JP | 2012-86037 | 5/2012 |
| WO | 2010/005109 | 1/2010 |

OTHER PUBLICATIONS

U.S. Appl. No. 14/383,292 to Yasushi Kawaguchi et al., filed Sep. 5, 2014.
U.S. Appl. No. 14/383,275 to Taiichiro Ida et al., filed Sep. 5, 2014.
Search report from International Patent Appl. No. PCT/JP2013/063232, mail date is Jun. 4, 2013.
Search Report issued by E.P.O. patent office in E.P.O. Patent Application No. 13800243.1, dated Dec. 23, 2015.
Zuomin Zhao et al., "Backward-mode photoacoustic transducer for sensing optical scattering and ultrasonic attenuation: determining fraction consistencies in pulp suspensions; Backward-mode photoacoustic transducer for sensing optical scattering and ultrasonic attenuation", Measurement Science and Technology, IOP, Bristol, GB, vol. 21, No. 2, Feb. 1, 2010, XP020174407, pp. 25105.
Office Action issued in China Family Member Patent Appl. No. 201380012448.9, dated Jul. 28, 2015.

* cited by examiner

Comparative Example (a)

Comparative Example (b)

PHOTOACOUSTIC WAVE MEASUREMENT DEVICE

FIELD OF THE INVENTION

The present invention relates to photoacoustic sensors.

BACKGROUND ART

Photoacoustic sensors are conventionally known to measure a photoacoustic signal generated by irradiating an object to be measured (e.g. biological object) with pulsed light (see, for example, Patent Document 1 (Japanese Unexamined Patent Publication No. 2011-229660)).

SUMMARY OF THE INVENTION

Such a photoacoustic signal obtained by the photoacoustic sensor, however, might have noise superimposed thereon.

Accordingly, it is an object of the present invention to reduce noise to be superimposed on the photoacoustic signal obtained by the photoacoustic wave measurement device.

According to the present invention, a photoacoustic wave measurement device includes: a pulsed-light outputter that outputs a pulsed light; an arrangement member disposed between a pulsed-light output end of the pulsed-light outputter and a measurement object, the arrangement member being adapted to allow the pulsed light to pass therethrough; and a photoacoustic wave detector that receives a photoacoustic wave generated by the measurement object by the pulsed light and that converts the photoacoustic wave into an electric signal, wherein the photoacoustic wave detector is farther from the measurement object than the pulsed-light output end, and the arrangement member has such a sufficient thickness that noise to be detected by the photoacoustic wave detector after a start time of detection of the photoacoustic wave starts to be detected after an end time of the detection of the photoacoustic wave.

According to the thus constructed photoacoustic wave measurement device, a pulsed-light outputter outputs a pulsed light. An arrangement member is disposed between a pulsed-light output end of the pulsed-light outputter and a measurement object, the arrangement member being adapted to allow the pulsed light to pass therethrough. A photoacoustic wave detector receives a photoacoustic wave generated by the measurement object by the pulsed light and converts the photoacoustic wave into an electric signal. The photoacoustic wave detector is farther from the measurement object than the pulsed-light output end. The arrangement member has such a sufficient thickness that noise to be detected by the photoacoustic wave detector after a start time of detection of the photoacoustic wave starts to be detected after an end time of the detection of the photoacoustic wave.

According to the photoacoustic wave measurement device of the present invention, the pulsed-light outputter may be an optical fiber.

According to the photoacoustic wave measurement device of the present invention, the photoacoustic wave detector may be a piezoelectric element.

MODES FOR CARRYING OUT THE INVENTION

A description will now be given of an embodiment of the present invention referring to drawings.

Figure 1:
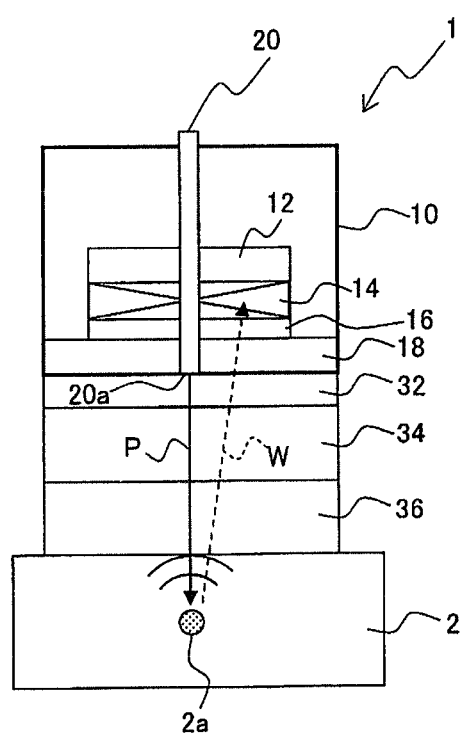
FIG. 1 is a cross-sectional view of a photoacoustic wave measurement device 1 according to one embodiment of the present invention.

FIG. 1 is a cross-sectional view of a photoacoustic wave measurement device 1 according to one embodiment of the present invention. The photoacoustic wave measurement device 1 includes a case 10, a backing member 12, a piezoelectric element (photoacoustic wave detector) 14, an electrode 16, a spacer 18, an optical fiber (pulsed light outputter) 20, and external spacers (arrangement members) 32, 34, and 36.

The case 10 is a case for accommodating therein the backing member 12, the piezoelectric element 14, the electrode 16, and the spacer 18. The spacer 18 is in contact with the bottom surface of the case 10, and the electrode 16 is mounted on the spacer 18. The piezoelectric element 14 is mounted on the electrode 16, and the backing member 12 is mounted on the piezoelectric element 14.

The backing member 12 serves as a backing material made of epoxy resin. The piezoelectric element (or photoacoustic wave detector) 14 receives a pressure caused by compression waves or the like and converts the pressure into a voltage. The electrode 16 receives the voltage from the piezoelectric element 14 and supplies the voltage to an external measurement device (e.g. an oscilloscope (not shown)). The electrode 16 is, for example, a gold electrode. The spacer 18 allows the compression waves to pass therethrough. The spacer 18 is a transparent spacer, for example, made of polystyrene.

The optical fiber (i.e. pulsed light outputter) 20 outputs a pulsed light P from a pulsed-light output end 20a. The optical fiber 20 is connected to a pulse light source (not shown) outside the photoacoustic wave measurement device 1. The optical fiber 20 penetrates through the case 10, the backing member 12, the piezoelectric element 14, the electrode 16, and the spacer 18.

The external spacers (i.e. arrangement members) 32, 34, and 36 are disposed between the pulsed-light output end 20a and a measurement object 2 so as to allow the pulsed light P to pass therethrough. The external spacer 32 is in contact with the case 10 and the pulsed-light output end 20a. The external spacer 36 is in contact with the measurement object 2. The external spacer 34 is disposed between the external spacer 32 and the external spacer 36.

The external spacer (i.e. arrangement member) 32 is a spacer, for example, made of white polycarbonate of 1.5 mm in thickness. Each of the external spacers (i.e. arrangement members) 34 and 36 is a transparent spacer made of polystyrene of 4.0 mm in thickness. Note that the external spacers 32, 34, and 36 may be integrally formed together.

The measurement object 2 is, for example, a finger cushion of a human being. The measurement object 2 includes a blood vessel 2a. When receiving the pulsed light P, the blood vessel 2a generates a photoacoustic wave W.

The piezoelectric element 14 receives the photoacoustic wave W and converts the wave W into an electric signal (for example, in the form of voltage). The piezoelectric element 14 is farther from the measurement object 2 than the pulsed-light output end 20a.

Next, the operation of the one embodiment in the present invention will be described by comparing with the comparative examples.

First, the pulsed light P emitted from an external pulsed light source (not shown) passes through the optical fiber 20, and then is output from the pulsed-light output end 20a. The pulsed light P is applied to the measurement object 2 through the external spacers 32, 34, and 36.

The pulsed light P reaches the blood vessel 2a of the measurement object 2. At this time, the blood vessel 2a absorbs the pulsed light P and is warmed and is then adiabatically expanded. Thus, the compression waves (i.e. photoacoustic waves W) are output from the blood vessel 2a.

The photoacoustic waves W reach the piezoelectric element 14 through the measurement object 2, the external spacers 36, 34, and 32, the spacer 18, and the electrode 16. The piezoelectric element 14 converts the pressure produced by the photoacoustic wave W into an electric signal (for example, in the form of voltage). The voltage is taken out to the outside via the electrode 16, and then fed to an oscilloscope or the like.

Figure 2A:
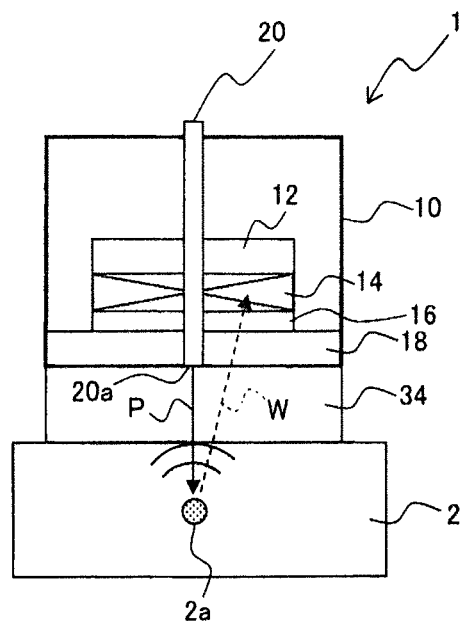
FIG. 2(a) shows a cross-sectional view of another photoacoustic wave measurement device 1 in a comparative example (a)
Figure 2B:
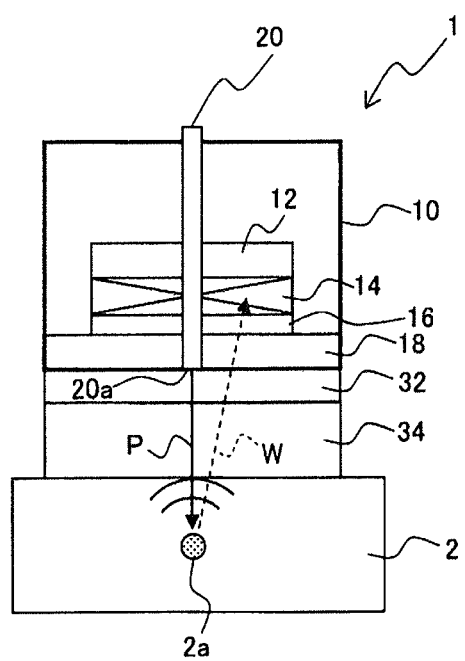
FIG. 2(b) shows a cross-sectional view of a further photoacoustic wave measurement device 1 in another comparative example (b)

FIG. 2(a) shows a cross-sectional view of another photoacoustic wave measurement device 1 in a comparative example (a), and FIG. 2(b) shows a cross-sectional view of a further photoacoustic wave measurement device 1 in another comparative example (b).

The comparative example (a) is one obtained by removing the external spacers 32 and 36 from the photoacoustic wave measurement device 1 shown in FIG. 1. The comparative example (b) is one obtained by removing the external spacer 36 from the photoacoustic wave measurement device 1 shown in FIG. 1.

Figure 3:
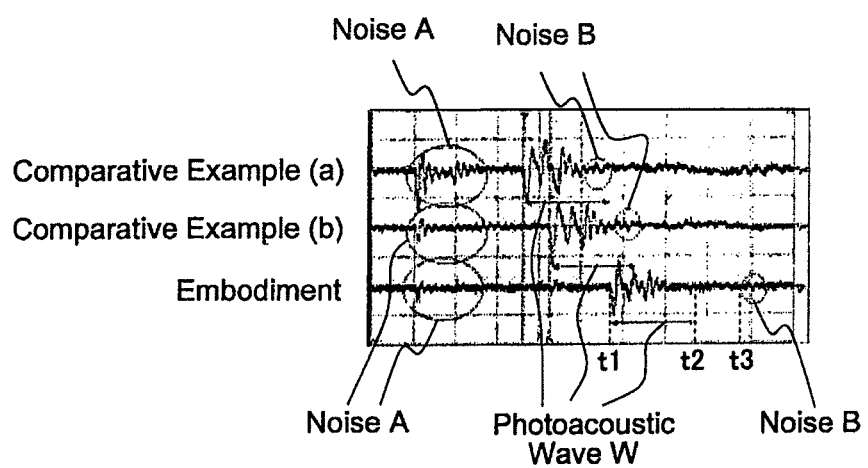
FIG. 3 shows a graph of waveforms detected by the photoacoustic wave measurement devices 1 in the comparative examples (a) and (b) (see FIGS. 2(a) and (b)), and by the photoacoustic wave measurement device 1 in the one embodiment of the present invention (see FIG. 1).

FIG. 3 shows a graph of waveforms detected by the photoacoustic wave measurement devices 1 in the comparative examples (a) and (b) (see FIGS. 2(a) and (b)), and by the photoacoustic wave measurement device 1 in the one embodiment of the present invention (see FIG. 1).

Each of the detected waveforms in the comparative examples (a) and (b) and the one embodiment of the present invention includes noise A, photoacoustic wave W, and noise B.

The photoacoustic wave W is a photoacoustic wave generated from the blood vessel 2a of the measurement object 2. The photoacoustic wave has a waveform which is to be detected. During a period of time indicated by a bidirectional arrow, the photoacoustic wave W is detected.

The noise A is noise detected by the piezoelectric element 14 before a time t1 when the photoacoustic wave W starts to be detected. In the embodiment of the present invention as well as comparative examples (a) and (b), the noise A is not superimposed on the photoacoustic wave W.

The noise B is noise detected by the piezoelectric element 14 after the time t1 when the photoacoustic wave W starts to be detected. In the comparative examples (a) and (b), the noise B is superimposed on the photoacoustic wave W due to insufficient thickness of the external spacer.

In the embodiment of the present invention, however, the noise B is not superimposed on the photoacoustic wave W. That is, in the embodiment of the present invention, a time t3 when the noise B starts to be detected comes after a time t2 of the end of detecting the photoacoustic wave W because of a sufficient thickness of the external spacers 32, 34, and 36.

The thicknesses of the external spacers in respective cases are as follows: [the thickness of the external spacer in the comparative example (a)]<[the thickness of the external spacer in the comparative example (b)]<[the thickness of the external spacer in the embodiment of the present invention]. As the thickness of the external spacer is increased, the time required for the photoacoustic wave W to reach the piezoelectric element 14 becomes longer. As a result, the detection start time of the photoacoustic wave W in the comparative example (b) is delayed more than that in the comparative example (a), whereas the detection start time of the photoacoustic wave W in the embodiment of the present invention is delayed more than that in the comparative example (b).

Further, the time when the noise B starts to be detected is delayed more as the thickness of the external spacer is increased. However, it has been newly found from the detected waveforms shown in FIG. 3 that the delay of the detection start time of the noise B due to the increase in thickness of the external spacer is much larger than the delay of the detection start time of the photoacoustic wave W.

This is supposed to be because the photoacoustic wave generated in the vicinity of the pulsed-light output end 20a is reflected by a boundary surface between the external spacer 36 and the measurement object 2 and then reaches the piezoelectric element 14 to cause the noise B. In this case, the detection start time of the noise B is delayed by a time that requires the wave W to travel about twice as long as the thickness of the external spacer.

In the photoacoustic wave measurement device 1 of the one embodiment of the present invention, the time t3 when the noise B starts to be detected comes after the time t2 of the end of detecting the photoacoustic wave W because of a sufficient thickness of the external spacers 32, 34, and 36. Accordingly, the present invention can reduce the noise to be superimposed on the photoacoustic signal obtained by the photoacoustic wave measurement device 1.

The invention claimed is:

1. A photoacoustic wave measurement device comprising:
   a pulsed-light outputter that outputs a pulsed light;
   an arrangement member disposed between a pulsed-light output end of the pulsed-light outputter and a measurement object, the arrangement member being adapted to allow the pulsed light to pass therethrough; and
   a photoacoustic wave detector that receives a photoacoustic wave generated in the measurement object by the pulsed light and that converts the photoacoustic wave into an electric signal, wherein
   the photoacoustic wave detector is farther from the measurement object than the pulsed-light output end, and
   the arrangement member has a thickness such that noise to be detected by the photoacoustic wave detector after a start time of detection of the photoacoustic wave starts to be detected after an end time of the detection of the photoacoustic wave.

2. The photoacoustic wave measurement device according to claim 1, wherein the pulsed-light outputter is an optical fiber.

3. The photoacoustic wave measurement device according to claim 1, wherein the photoacoustic wave detector is a piezoelectric element.

* * * * *